US008449902B2

(12) United States Patent
Brown et al.

(10) Patent No.: US 8,449,902 B2
(45) Date of Patent: May 28, 2013

(54) METHODS FOR PRODUCING BIOMATERIALS WITH VARIABLE STIFFNESS

(75) Inventors: Robert Brown, Middlesex (GB); Ektors Hadjipanayi, Middlesex (GB)

(73) Assignee: UCL Business PLC, London (GB)

( * ) Notice: Subject to any disclaimer, the term of this patent is extended or adjusted under 35 U.S.C. 154(b) by 0 days.

(21) Appl. No.: 12/667,363

(22) PCT Filed: Jul. 7, 2008

(86) PCT No.: PCT/GB2008/002307
§ 371 (c)(1),
(2), (4) Date: Dec. 30, 2009

(87) PCT Pub. No.: WO2009/004351
PCT Pub. Date: Jan. 8, 2009

(65) Prior Publication Data
US 2010/0183698 A1    Jul. 22, 2010

(30) Foreign Application Priority Data

Jul. 5, 2007    (GB) .................................. 0713079.2

(51) Int. Cl.
A61L 27/00    (2006.01)
A61K 35/12    (2006.01)
A61K 9/00    (2006.01)
C12N 5/08    (2006.01)
A61P 41/00    (2006.01)

(52) U.S. Cl.
USPC ............ 424/423; 435/1.1; 435/374; 435/397; 435/377

(58) Field of Classification Search
None
See application file for complete search history.

(56) References Cited

U.S. PATENT DOCUMENTS
4,689,399 A    8/1987    Chu

FOREIGN PATENT DOCUMENTS
WO    WO 2006/003442    1/2006

OTHER PUBLICATIONS

Brown et al., Ultrarapid engineering of biomimetic materials and tissus: fabrication of nano- and microstructures by plastic compression, Adv. Funct. Mater. 2005, 15, 1762-1770.*
Gray et al., Repositioning of cells by mechanotaxis on surfaces with micropatterned Young's modulus, J Biomed Mater Res 66A: 605-614,2003.*
MacDonald et al., Collagen—carbon nanotube composite materials as scaffolds in tissue engineering, Published online Jun. 22, 2005 in Wiley InterScience (www.interscience.wiley.com), J Biomed Mater Res 74A: 489-496, 2005.*
Brown et al., "Ultrarapid Engineering of Biomimetic Materials and Tissues: Fabrication of Nano- and Microstructures by Plastic Compression," *Advanced Functional Materials*, 15(1):1762-1770, 2005.

* cited by examiner

*Primary Examiner* — James Ketter
*Assistant Examiner* — Reza Ghafoorian
(74) *Attorney, Agent, or Firm* — Klarquist Sparkman, LLP

(57) ABSTRACT

This invention relates to the production of biomaterials with variable stiffness by subjecting a gel which varies in at least one dimension to plastic compaction. These biomaterials may be useful, for example, for the directional control or guidance of cells within tissue equivalent implants.

21 Claims, 4 Drawing Sheets

METHODS FOR PRODUCING BIOMATERIALS WITH VARIABLE STIFFNESS

CROSS REFERENCE TO RELATED APPLICATIONS

This is the U.S. National Stage of International Application No. PCT/GB2008/002307, filed Jul. 7, 2008, which was published in English under PCT Article 21(2), which in turn claims the benefit of GB 0713079.2, filed Jul. 5, 2007. The provisional application is incorporated herein in its entirety.

This invention relates to the modulation of stiffness and density in tissue equivalent implants and tissue scaffolds, for example for use in the repair and/or replacement of damaged tissue in an individual or the fabrication of tissue equivalent 3D models for in vitro testing, screening or diagnosis.

As biomimetic materials are designed for ever more subtle and complex forms of cell-tissue control and systems mimicry, new modes of control or guidance are required. In addition, it becomes necessary to fabricate more subtle features of tissue structure and to identify the means to construct these structures, particularly by means which do not harm the resident cells.

Durotaxis is a phenomenon described in biological terms as cells tend to move preferentially from softer to stiffer substrates (Jiang et al, 2006 Biophysical J. 90 1804-1809; Lo et al 2000 Biophysical J. 79 144-152). Stiffness (durotactic) gradients may be useful for control or guidance of cells in one or more particular desired directions in tissue engineering and repair biology and may offer significant advantages over known cell guidance techniques such as biochemical gradients or surface topography.

The present invention relates to the finding that the stiffness of tissue equivalent implants can be conveniently modulated to produce implants with defined stiffness (hence durotactic) gradients by varying the density of a biomaterial through plastic compaction of gels of particular shapes.

One aspect of the invention provides a method of producing a biomaterial with variable stiffness comprising:
  providing a gel having a dimension which is greater at a first region than at a second region,
  plastically compacting the gel, such that the difference in the dimension of the gel at the first and second regions is reduced, thereby producing the biomaterial,
  wherein the biomaterial has increased stiffness in the first region relative to the second region.

The dimension of the gel which is plastically compacted to produce the biomaterial is referred to herein as thickness. The gel may be compacted in any orientation and the thickness of the gel at the first and second regions may be less than, the same as, or greater than one or both of the other two dimensions of the gel (i.e. the width and height of the gel). Gels for use as described herein thus have a variable thickness and are plastically compacted into biomaterials having variable stiffness.

Preferably, the gel is compacted such that the difference in the thickness of the gel between the first region and the second region of the gel is abolished i.e. the thickness of the compacted gel is the same at the first and second regions. The biomaterial which is produced by the compaction may thus possess a uniform thickness but a variable material density. The density at any point in the biomaterial is shown herein to reflect the stiffness of the biomaterial.

In some embodiments, the thickness of the gel progressively increases from the first region to the second region of the gel, such that the stiffness of the biomaterial produced by compaction increases progressively from the first region to the second region i.e. the biomaterial displays a stiffness gradient between the first and second regions. A method of producing a biomaterial with variable stiffness may comprise:
  providing a gel having a dimension which increases progressively from a first region to a second region,
  plastically compacting the gel, such that the difference in the dimension of the gel at the first and second regions is reduced, thereby producing the biomaterial,
  wherein the stiffness of the biomaterial increases progressively from the first region to the second region.

In some embodiments, the dimension of the gel may increase continuously from the first region to the second region of the gel, such that the stiffness of the biomaterial which is produced increases continuously from the first region to the second region (i.e. a continuous stiffness gradient). The dimension of the gel may increase in a linear fashion to produce a biomaterial with a linear stiffness gradient, or in a non-linear fashion to produce a biomaterial with a non-linear stiffness gradient, for example a curved or stepped stiffness gradient.

In other embodiments, the dimension of the gel may both increase and decrease between the first and second regions of the gel, such that the stiffness of the biomaterial which is produced increases and decreases between the first and second regions. For example, the biomaterial may comprise islands of high stiffness surrounded by regions of low stiffness or vice versa.

The shape of the stiffness gradient in the biomaterial may be controlled by the shape of the gel prior to compaction. By casting the initial gel in a shaped chamber, it is possible to generate gels with complex shapes (e.g. a curved profile) which, after plastic compaction, produce biomaterials with complex stiffness gradients which reflect the original complex gel shape (i.e. the stiffness of the biomaterial at a particular point is directly related to the thickness of the original gel at that point).

The gel may vary in a second and/or third dimension (i.e. width and height) in different regions of the gel. The gel may be further plastically compacted in the second and/or third dimensions to produce further variations in stiffness within the biomaterial. This allows the production of increasing levels of hierarchical complexity, as required.

Typically, the gradient or pattern of stiffness in the biomaterial is selected to mimic a particular tissue structure. The methods described herein provide a controllable fabrication process which allows any desired structure to be mimicked.

Gels comprise a matrix of scaffold fibres and an interstitial fluid. Gels are formed by the coalescence and elongation of scaffold fibrils, as the fibrils form a continuous network around the aqueous interstitial liquid which originally held the monomers. For example, triple helical collagen monomers may be initially dissolved in dilute acid and then induced to polymerise (aggregate) to fibrils (e.g. at 37° and neutral pH). As the fibrils polymerise, there is a phase change and the solid network of fibrils 'supports' the remaining interstitial liquid in approximately the same volume and shape— i.e. it gels. Phase transition from soluble monomer to solid polymer is characteristic of a gel and is important in providing the properties described herein. Gels are distinct from 'sponges', which may be formed from pre-polymerised fibres.

Any hydrated polymer material may be suitable for use in the gels described herein, including naturally occurring polymers, for example proteins, such as silk, fibrin, fibronectin, elastin or collagen (e.g. collagen type I), glycoproteins such as fibronectin, or polysaccharides such as chitin, or cellulose. In some preferred embodiments, the scaffold fibres are made collagen. Native fibril forming collagen types are preferred including collagen types are I, II, III, V, VI, IX and XI and combinations of these (e.g. I, III V or II, IX, XI). For example, a collagen type I may be used as the scaffold material.

Other suitable fibrous scaffold materials include synthetic polymers i.e. polymers that are not naturally present in the human or animal body. Suitable polymers include organic polymers such as polylactone, polyglycone and polycaprylolactone, inorganic polymers such as phosphate glass and synthetic, gelling polypeptide gels.

In some embodiments, the fibrous scaffold material may be a composite material comprising two or more different types of fibre. For example, the scaffold may comprise fibronectin and collagen, collagen and polylactide, fibrin and collagen, collagen fibres and carbon-nanotubes, or fibrin, collagen and fibronectin.

The interstitial liquid in a gel is typically an aqueous liquid which acts as a solvent for the soluble collagen fibre. For example, the liquid may be water with solutes such as salts and proteins dissolved therein. In some embodiments, the interstitial liquid is a cell culture medium suitable for the growth and proliferation of cells.

Techniques for formulating and casting gels for use as biomaterials are well-known in the art (see, for example, WO2006/003442; WO2007/060459; Marenzana et al 2006 Exp Cell Res 312 423-433; Tomasek et al (2002) Nat Rev Mol Cell Biol 3 349-363; Harris et al Nature 290 (1981) 249-251; Elsdale et al 1972 J Cell Biol. 54 626-637; Kolodney et al J Cell Biol. (1992) 117 73-82; Eastwood et al Biochem Biophys Acta 1201 (1994) 186-192).

In preferred embodiments, the gel may be cast into a shape in which at least one of the three dimensions of the gel (termed 'thickness herein) varies in relation to one or both of the other dimensions. For example, the thickness of the cast gel may vary across the width and/or length of the gel.

This may be achieved by any convenient technique. For example, the mould may be tilted when the gel is cast such that a wedge shaped gel is produced by the effect of gravity; a gel may be cast in a shaped mould; or a gel may be cast in more than one piece and then assembled prior to compaction, optionally with pieces of more than one different material.

After casting, the gel may be orientated such that it is subjected to plastically compaction in the dimension which varies relative to one or both other dimensions as described herein, to produce a biomaterial with variable stiffness.

Plastic compaction involves deforming an object such as a gel to reduce its volume, such that the object substantially retains its new volume, even after the cause of compaction is removed. Plastic compaction is a rapid, cell-independent process which results from subjecting the gel to a physical treatment, such as an external force or pressure, which expels interstitial liquid from the gel, such that it does not return on removal of the load: i.e. the gel undergoes a plastic compaction. In an untreated gel, the scaffold matrix is generally in a gross, hydrated form. This scaffold structure collapses during plastic compaction without loss of structural detail, dehydrating the scaffold in the gel, and leading to increased density and strength.

Plastic compaction is distinct from the slow process of cell-driven contraction, which occurs through the intrinsic action of cells growing within the gel i.e. plastic compaction is not cell-mediated and does not occur through the action of cells which are cultured within the gel. Plastic compaction has a vector in one, two or more defined directions and the direction, rate and extent of the compaction is controllable.

The vector(s) of compaction can also be used to control the density/stiffness gradient.

The amount or extent of compaction may be varied, depending on the intended use of the biomaterial. Compaction of the gel, for example by compression, may result in a reduction in the thickness of the gel of at least 5 fold, at least 10 fold or at least 20 fold. The compacted dimension of the gel may be reduced by 200 fold or less, 150 fold or less or 100 fold or less. For example, the volume of the gel may be reduced by 50% or more, 60% or more, 70% or more, 80% or more, 90% or more, 95% or more, 99% or more, or 99.9% or more by plastic compaction The variation in thickness of the gel results in a different amount of compaction in different parts of the gel. Thicker parts of the gel undergo more compaction and therefore become denser than thinner parts of the gel.

The time required for compaction will be less than the time required for cell-driven contraction to occur and will vary in accordance with the compaction method and the conditions used. For example, compaction may occur in less than 12 hours, less than 6 hours, less than 3 hours, less than 1 hour, less than 30 minutes or less than 10 minutes. In some preferred embodiments, the gel may be compacted in 2 minutes or less, or 1 minute or less.

Plastic compaction of the gel may be associated with the loss or removal of some or all of the interstitial fluid from said gel. For example, the amount of fluid lost or removed from the gel by plastic compaction may be at least 50%, at least 60%, at least 70%, at least 80%, at least 90%, at least 99%, or at least 99.9% of the original fluid content of the gel.

Preferably, some interstitial fluid remains after compaction, for example at least 10%, at least 1% or at least 0.1% of the original fluid content of the gel. In preferred embodiments, the gel is not subjected to drying or desiccation, for example heat-, freeze-, airflow or vacuum drying, following plastic compaction, as dehydration kills cells and damages biomaterial structure.

Plastic compaction may expel interstitial liquid from the gel or draw interstitial liquid out of the gel. More than one method may be used to compact the gel, either sequentially or simultaneously. Methods and means of plastic compaction are described in WO2006/003442.

The plastic compaction process may be optimised to achieve the desired final ratio of collagen, cells and channel forming inserts from a standard starting gel. A standard gel, for example, may comprise 1 to 4% collagen, 0.2 to $10 \times 10^6$ cells per ml and 0.2 to 2% channeling fibres or granules.

When cells are seeded within the scaffold of the gel, the gel environment is preferably maintained at physiological conditions (e.g. temperature, pH, hydration and ionic strength) for the cells to survive. In such biotic embodiments, it is preferred that plastic compaction does not alter the ionic properties of the gel fluid significantly from physiological conditions.

In abiotic embodiments, when the gel does not contain cells, the gel environment need not be physiological and any method of plastic compaction is suitable, including those that alter the ionic properties of the gel fluid, such as osmotic methods.

In preferred embodiments, the gel is seeded with cells, in particular human or other mammalian cells. In preferred embodiments, the cells are motile cells. These cells remain viable when the gel is compacted into the biomaterial. The gel may comprise cells that confer tissue functionality and provide structures which replace or facilitate the repair of endogenous tissue. For example, the gel may comprise one or more of muscle cells to provide contractile structures, vascular and/or neural cells to provide conductive elements, metabolically active secretory cells, such as liver cells, hormone synthesising cells, sebaceous cells, pancreatic islet cells or adrenal cortex cells to provide secretory structures, stem cells, such as bone marrow-derived or embryonic stem cells, dermal fibroblasts, skin keratinocytes, (and combination layers of the two), Schwann cells for nerve implants, smooth muscle cells and endothelial cells for vessel structures, urothelial and smooth muscle cells for bladder/urethra structures and osteocytes, chondrocytes, and tendon cells for bone and tendon structures. In some embodiments, the cells seeded into the gel may include fibroblasts and neural cells.

The cells may be seeded into the gel before compaction, for example when the gel is cast. Cells may be seeded within the matrix by mixing them with the liquid collagen and then allowing the liquid collagen to solidify into a gel. Seeding of the matrix is preferably performed under suitable conditions of temperature, pH, ionic strength and sheer to maintain viability, prior to gel formation.

In some preferred embodiments, cells are seeded uniformly throughout the gel before plastic compaction.

Plastic compaction as described herein of a gel uniformly seeded with cells generates a cell-density gradient in the compacted gel which corresponds to the collagen density gradient.

In some circumstances, variations in cell density may be required which do not correspond to the variations in collagen density which are produced by plastic compaction as described herein. For example, a biomaterial may be required with a high concentration of cells at a region of the gel where collagen density is low, and a low concentration of cells at a region where collagen density is high (i.e. the opposite of the distribution which naturally results from plastic compaction from a gel with a uniform cell distribution).

Such variations in cell density may be achieved by any convenient technique.

In some embodiments, an unset collagen gel may be provided which is seeded with a uniform distribution of cells and raising the first region of the gel relative to the second region, for example by tilting the gel, such that cells in the gel to gravitate from the first region to the second region.

Preferably, the unset gel is maintained at 4° C. during this process to prevent setting.

An unset gel may comprise a solution of collagen fibres in an interstitial liquid. The unset gel may be retained in a mould or cast which defines the shape of the gel after setting.

Once the required cell distribution is achieved (e.g. increased cell density at the second region), the gel is allowed to set, for example by warming the unset gel e.g. to 37° C. The set gel may then be used in a method described herein.

In other embodiments, cells may be injected directly into one end of the gel before or during setting to achieve variations in cell density.

Cells in a compacted biomaterial are susceptible to desiccation. To reduce cell death and/or damage associated with desiccation, the gel may be compacted in an aqueous liquid, for example a culture medium, such as DMEM, Ham's or Eagle's medium or a physiological buffer such as Ringer's or PBS. For non-cellular biomaterials, any solvent compatible with the scaffold matrix may be used.

Cells are also susceptible to hypoxic cell death and/or damage due to the high cell densities within the compacted biomaterial. To reduce and/or prevent cell death or damage, an implant or biomaterial may be stored under conditions which maintain viability but which do not support cell growth, until ready for use. For example, the implant or biomaterial may be stored at low temperature, such as 0° C. to 5° C., preferably 4° C.

In addition to the scaffold, cells and interstitial liquid, the gel may include further components. In particular, the gel may comprise solid elements, for example capillary filaments or porous beads Capillary filaments may be insoluble or soluble fibres of a rigid, solid polymer. Suitable filaments are preferably less than about 100 µm in diameter.

Soluble filaments inserted within the gel may dissolve to form capillary channels within the gel. These capillary channels within the gel may be useful for example, for one or more of: perfusion, drug and/or gene and/or media delivery into the scaffold; and anastomosis with a recipient's circulation.

Suitable soluble filaments may be made from soluble phosphate glass, polycapryolacetone, polyacetate, polyglycolic acid, silks, polysaccarides, or fused or crystallised salts.

Insoluble filaments may be useful for delivering optical therapies, optical monitoring, signal transmission and/or strain detection. Suitable insoluble filaments may be made from glass.

Capillary filaments may be inserted between the layers of a gel, added to the gel before casting or may be inserted into the gel after casting. In embodiments comprising more than one cast gel, the filaments may, for example, be sandwiched between the gels.

In some embodiments, the gel may comprise porous beads. Plastic compaction of the gel matrix forces fibres of the scaffold into pores of the porous beads to provide a tightly bonded structure. This may be useful, for example, when seeded with osteoblasts or chondrocytes, as artificial bone or calcified cartilage substitute tissues. Suitable porous beads may be approximately 100-500 microns in diameter and may be of any solid material, for example porous ceramic, glass, phosphate glass, hydroxapatite, or bone mineral preparations (from native bone removal of organic phase).

The ratio of granules:gel:cells will depend on the particle size and the tissue properties required (e.g. dense or loose packed hard tissue).

The properties of the collagen matrix are important in determining how the repair or regeneration of tissue is organised by cells and the initial scaffold structure effectively dictates most of the later downstream 3D structure. For many applications, it is therefore useful for the cells and fibres in a tissue equivalent implant to be aligned.

Cells and/or fibres of the scaffold matrix may be aligned, for example by applying tension across the gel. Tension may be applied before, during and/or after plastic compaction.

The tension is preferably uniaxial and the gel may be subjected to 5-50% uniaxial strain, preferably 10-30% uniaxial strain. The fibres and, if present, seeded cells, align in a parallel orientation to the direction of principle strain.

For example for a collagen gel, a strain of 5 to 30%, preferably 20-25% may be employed. In some embodiments, the compacted gel may be subjected to repeated cycles of uniaxial tensile loading as described in WO2007/060459 to improve its mechanical properties. Repetitive cycles of loading increase the fusion of collagen fibrils in a compacted collagen gel to produce a biomaterial which has improved material strength (i.e. increased break stress, break strain and/or elastic modulus).

A biomaterial produced by the present methods may be used without additional processing in the production of a tissue equivalent implant for the repair or replacement of damaged tissue.

A tissue equivalent implant is a device for implantation into an individual to repair or replace endogenous tissue, which, for example, may be damaged or diseased. Examples of diseased tissues which may be repaired or replaced by tissue equivalent implants include nerve, tendons, cartilage, skin, bone, urogenital elements, liver, cardiopulmonary tissues, kidney, ocular tissues, blood vessels, intestine, and glands.

Durotactic gradients, as described herein, may be especially useful in the stems of prosthetic orthopaedic implants, the centre and edges of skin wound dressings, nerve repair guides or spinal regeneration implants, guided vascular capillary in-growth, anti-adhesion, post surgery films and/or vascular wall implants.

Additional processing of the biomaterial may be performed to produce a tissue equivalent implant for the repair or replacement of damaged tissue. The biomaterial may, for example, be moulded and/or shaped to produce a tissue equivalent implant. The biomaterial may be moulded into a predetermined shape and/or may be subjected to further plastic compaction or tensioning which may be symmetrical or asymmetrical. The biomaterial may be shaped, cut or moulded into any convenient implant form, for example, a patch, block, tube, tape, strip, ring, toroid, capillary, roll, sheet or thread. The final shape of the tissue equivalent implant will depend on the particular context in which it is to be used. In some embodiments, the tissue equivalent implant may have a pliable form which is suitable for further shaping.

The tissue equivalent implant is preferably fixable at a site of tissue damage. For example, the implant may be fixable such that the entry end is located adjacent the proximal stump of a damaged tissue and the exit end is located adjacent the distal stump of a damaged tissue. The tissue equivalent implant may be fixed by any convenient technique. For example, it may be sutured or glued in place.

Another aspect of the invention provides a method of treatment of a damaged tissue in an individual comprising;
  producing a tissue equivalent implant using a method described herein and,
  fixing said implant to said damaged tissue to repair and/or replace said tissue.

Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures and tables described below.

EXPERIMENTS

Cells were cast and seeded as described previously (WO2006/003442; WO2007/060459; Eastwood et al Biochem Biophys Acta 1201 (1994) 186-192).

Figure 1:
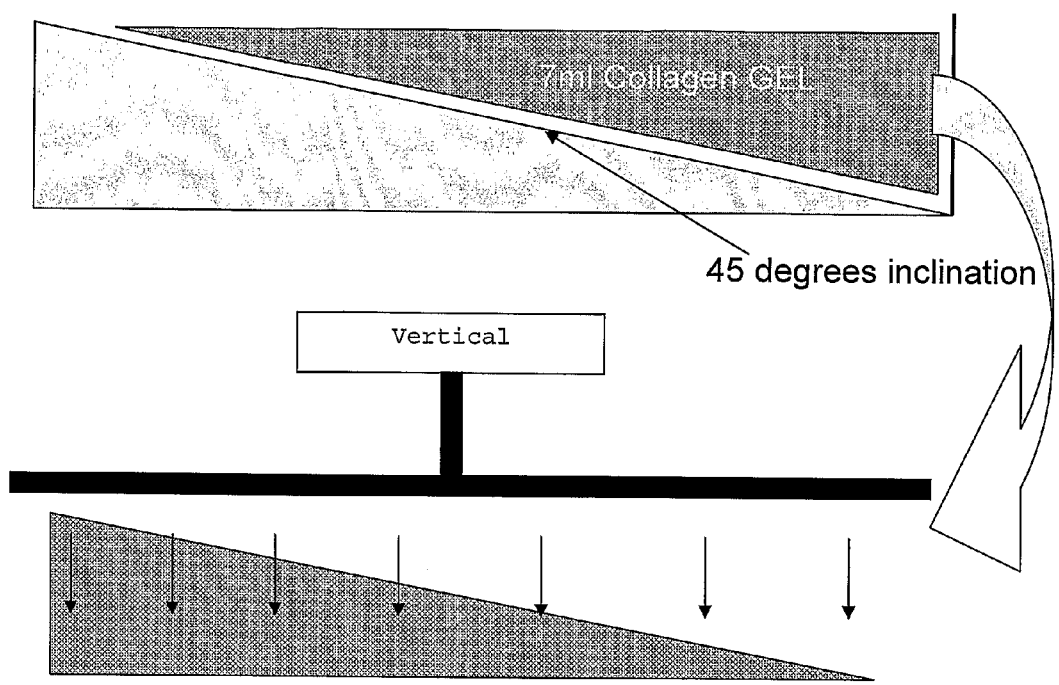
FIG. 1 shows a diagram of a casting wedge shaped collagen gel (upper) for compression into gradients (lower).
Figure 2:
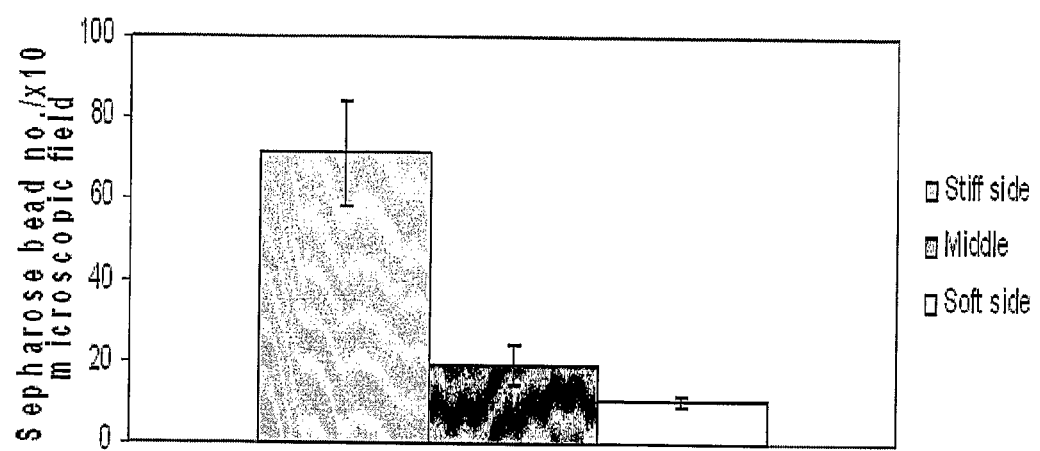
FIG. 2 shows the concentration of sepharose beads in a 7 ml collagen gel with a linear density/stiffness gradient seeded with 0.15 ml of 1 g/5 ml sepharose beads and subjected to plastic compaction to 0.7 mm (n=3).

Density variation within compacted gels was assessed by seeding standard blue sepharose beads homogeneously into the gels at the time of casting in the same way as cells are seeded. After plastic compaction, the gels were viewed microscopically and the beads counted in the 'stiff', middle and 'soft' ends (mean bead number per field). The increase in sepharose bead number per field shows the gradient of density within the gel after compaction (FIG. 2). The heavy beads tend to settle slightly during the gelling period (~5 min) and this tends to concentrate beads slightly towards the thick (ultimately denser) end due to the geometry of the wedge.

Figure 3:
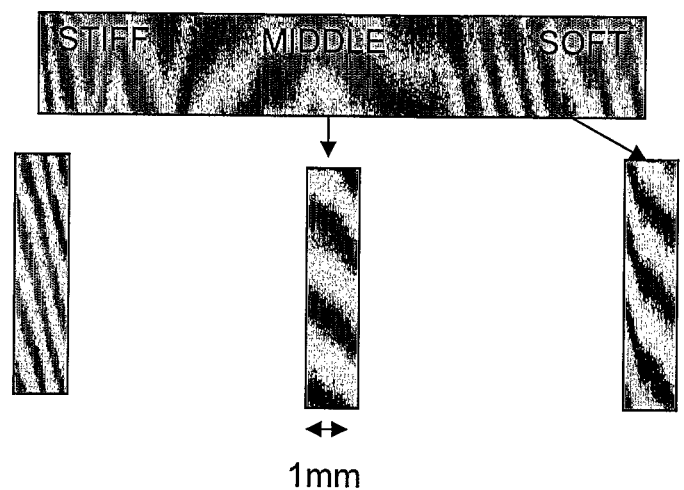
FIGS. 3 and 4 show dynamic mechanical analysis (DMA) (Perkin-Elmer DMA instrument) of a collagen gel with a continuous stiffness gradient seeded with 0.15 ml of 1 g/5 ml sepharose beads and subjected to plastic compaction.
Figure 4:
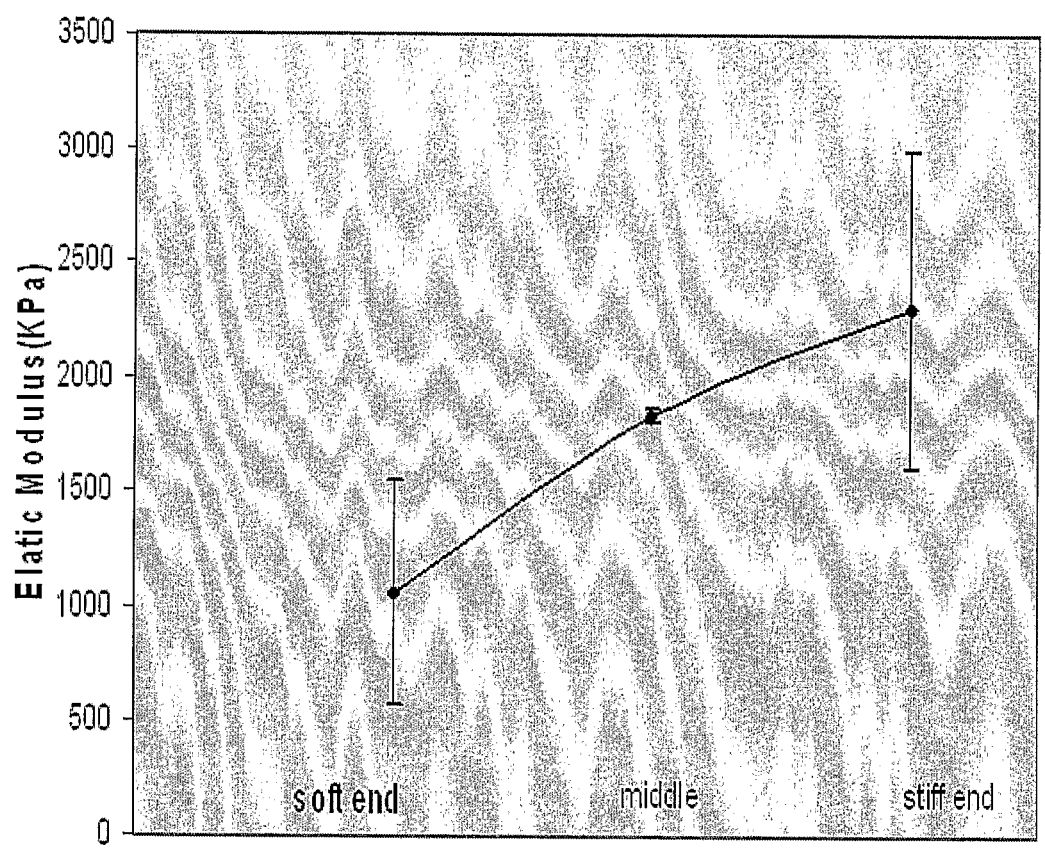

DMA analysis was performed using samples of the compacted gel from the 'stiff', middle and 'soft' ends as shown in FIG. 3. This analysis showed that the settling effect observed with the beads was not seen in the measured stiffness, which was close to linear, as the collagen fibrils are nm in diameter and cannot settle in the same way as the beads. From FIG. 4 it is clear that the actual material stiffness of the compacted gel increased along the material in the predicted manner, increasing by over 2 fold over the gel length, comparable with the density, as measured by Sepharose bead density, but in this case in a near linear manner (FIG. 4).

The invention claimed is:

1. A method of producing a biomaterial having a stiffness gradient, the method comprising:
  casting a collagen gel which is thicker at a first region than at a second region,
  plastically compacting the collagen gel such that the difference in the thickness of the gel at the first and second regions is reduced, thereby producing the biomaterial,
  wherein the biomaterial displays a stiffness gradient between the first region and the second region.

2. The method according to claim 1 wherein the thickness of the collagen gel is the same at the first and second regions following the plastic compaction.

3. The method according to claim 1 wherein the thickness of the gel progressively increases from the first region to the second region, such that the stiffness of the biomaterial progressively increases from the first region to the second region.

4. The method according to claim 3 wherein the thickness of the gel continuously increases from the first region to the second region of the gel, such that the stiffness of the biomaterial continuously increases from the first region to the second region.

5. The method according to claim 4 wherein the thickness of the gel increases linearly from the first region to the second region of the gel, such that the stiffness of the biomaterial increases linearly from the first region to the second region.

6. The method according to claim 1 wherein the gel is seeded with viable cells before plastic compaction.

7. The method according to claim 6 wherein the viable cells are selected from the group consisting of muscle cells, liver cells, kidney cells, heart cells, lung cells, gut cells, bronchial cells, ocular cells, reproductive cells, vascular cells, neural cells, secretory cells, stem cells, fibroblasts, Schwann cells, smooth muscle cells, endothelial cells, urothelial cells, osteocytes, chondrocytes, and tendon cells.

8. The method according to claim 6 wherein plastic compaction of the gel produces an increased cell density at the first region of said gel relative to the second region of said gel.

9. The method according to claim 6 wherein the cells are allowed to gravitate towards the second region of the gel before plastic compaction.

10. The method according to claim 9 wherein plastic compaction produces an increased cell density at the second region relative to the first region.

11. The method according to claim 1 wherein the fibrils of the gel are aligned by applying uniaxial tension to the gel.

12. The method according to claim 11 wherein the uniaxial tension is applied before plastic compaction.

13. The method according to claim 1 comprising implanting the biomaterial in a human or animal body for the repair or replacement of damaged tissue.

14. The method according to claim 1 comprising moulding or shaping the biomaterial to produce a tissue equivalent implant.

15. The method according to claim 14 comprising folding or rolling the biomaterial to produce the implant.

16. The method according to claim 14 wherein the biomaterial is subjected to further plastic compaction to produce the implant.

17. A method of treatment of a damaged tissue in an individual comprising: fixing a tissue equivalent implant to said damaged tissue to repair and/or replace said tissue, wherein the tissue equivalent implant comprises a biomaterial produced by the method of claim 1.

18. The method according to claim 17 wherein the damaged tissue results from arthritides, neuro-muscle injury/degeneration, musculotendenous failure and age-degeneration, poor regeneration after trauma, tissue necrosis or surgical resection.

19. The method according to claim 1 wherein the gel further comprises carbon nanotube co-fibres.

20. A method of producing a biomaterial having a stiffness gradient, the method comprising:

casting a collagen gel which is thicker at a first region than at a second region, seeding the collagen gel with viable cells, allowing the cells to gravitate towards the second region of the gel, and plastically compacting the collagen gel seeded with viable cells, such that the difference in the thickness of the gel at the first and second regions is reduced, thereby producing the biomaterial, wherein the biomaterial displays a stiffness gradient between the first region the second region.

21. The method according to claim 20, wherein the plastic compaction produces an increased cell density at the second region relative to the first region.

* * * * *